United States Patent [19]

Draggoo et al.

[11] Patent Number: 4,868,768
[45] Date of Patent: Sep. 19, 1989

[54] OPTICAL ABSORPTION MEASUREMENT SYSTEM

[75] Inventors: Vaughn G. Draggoo, Livermore; Richard G. Morton, San Diego; Richard H. Sawicki, Pleasanton; Horst D. Bissinger, Livermore, all of Calif.

[73] Assignee: The United States of America as represented by the United States Department of Energy, Washington, D.C.

[21] Appl. No.: 908,482

[22] Filed: Sep. 17, 1986

[51] Int. Cl.$^4$ .............................................. G01J 5/08
[52] U.S. Cl. .................................... 364/525; 364/524; 356/51; 250/330; 250/341
[58] Field of Search .................. 364/524, 525, 557; 250/330, 332, 334, 341, 342; 374/124, 32; 356/432 T, 43, 51

[56] References Cited

U.S. PATENT DOCUMENTS

| | | | |
|---|---|---|---|
| 3,635,085 | 1/1972 | Shimotsuma et al. | 250/330 |
| 4,429,999 | 2/1984 | Bimberg et al. | 250/341 |
| 4,468,136 | 8/1984 | Murphy et al. | 250/334 |
| 4,576,485 | 3/1986 | Lambert | 374/130 |
| 4,607,341 | 8/1986 | Monchalin | 364/557 |
| 4,682,222 | 7/1987 | Smith et al. | 250/334 |

Primary Examiner—Parshotam S. Lall
Assistant Examiner—Ellis B. Ramirez
Attorney, Agent, or Firm—William J. Egan, III; Clifton E. Clouse, Jr.; William R. Moser

[57] ABSTRACT

The system of the present invention contemplates a non-intrusive method for measuring the temperature rise of optical elements under high laser power optical loading to determine the absorption coefficient. The method comprises irradiating the optical element with a high average power laser beam, viewing the optical element with an infrared camera to determine the temperature across the optical element and calculating the absorption of the optical element from the temperature.

11 Claims, 3 Drawing Sheets

ABSORPTION DATA FOR SELECTED COATING TYPES

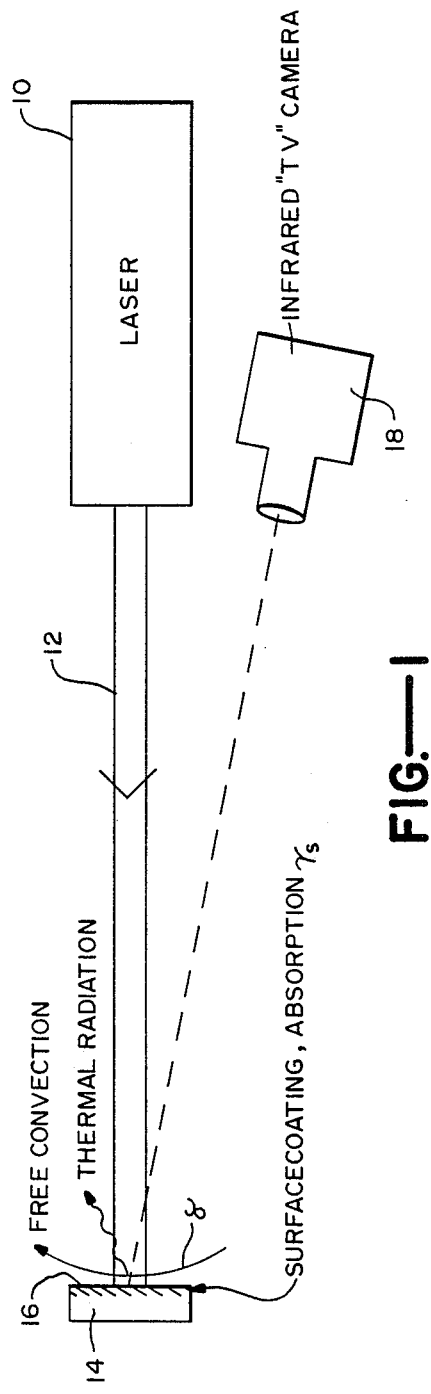
FIG.—1
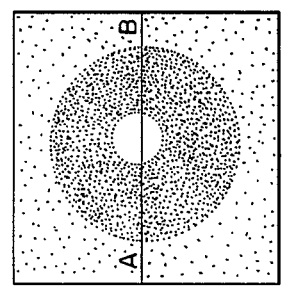
FIG.—2
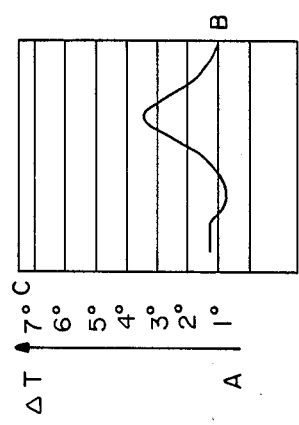
FIG.—3

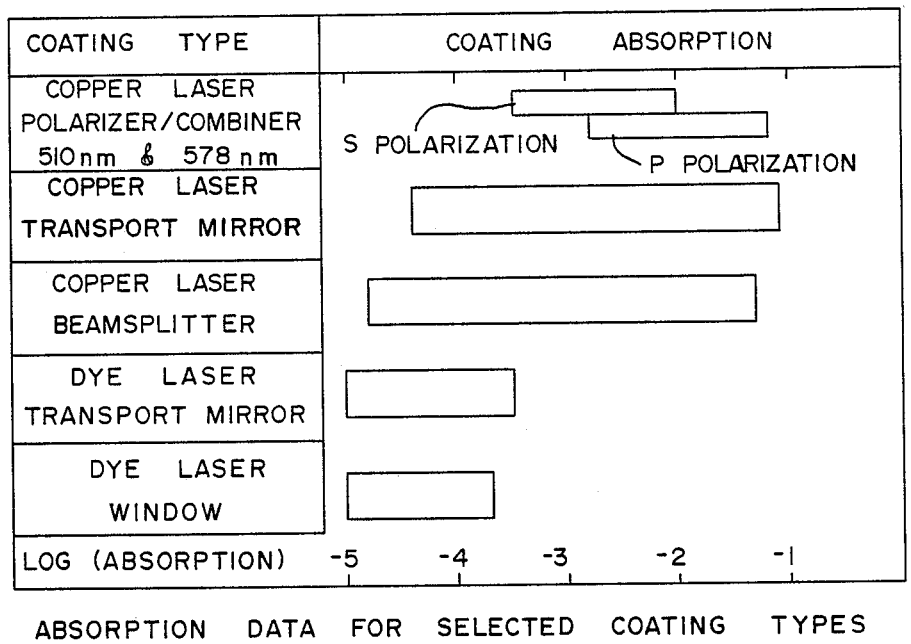
ABSORPTION DATA FOR SELECTED COATING TYPES
FIG.—4

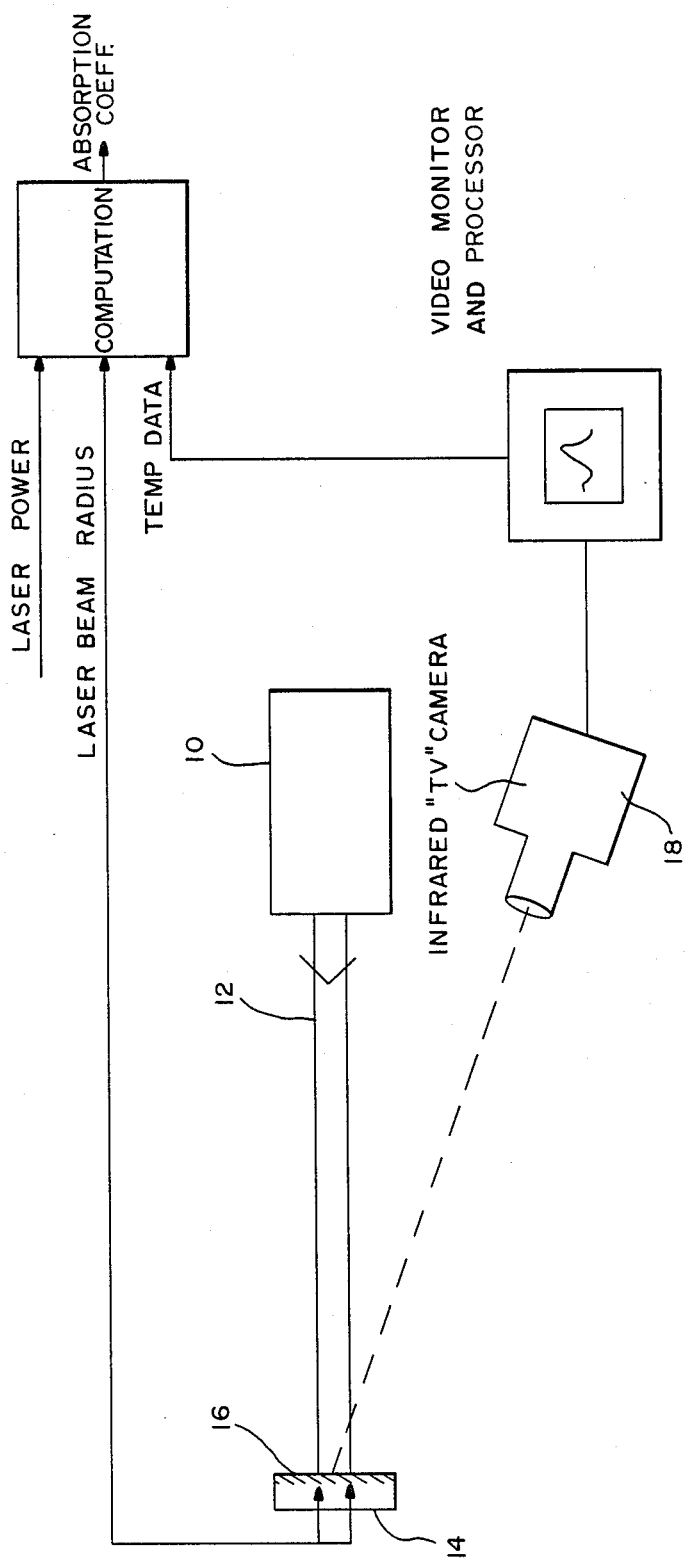
FIG.—5

OPTICAL ABSORPTION MEASUREMENT SYSTEM

The present invention relates to measuring optical absorption, and more particularly, to a system for remotely sensing the optical absorption in optical elements being irradiated with high average power laser light.

Optical absorption in optical elements, such as windows, prisms, lenses, and mirrors, is an important design consideration in the development of a high average power laser-optical systems, e.g. 100 to 10,000 watt systems. At high average power, the fraction absorbed on either the surface or in the bulk substrate material of an optical element or component may be large enough to induce wavefront aberrations because of thermal stress/strain or refractive index variations. If the absorption is too large, it can result in catastrophic failure of the optical coating or substrate. Clearly, optimum system performance can only be achieved through careful thermal design, which requires accurate and reliable measurement of the thermal characteristics of the optical coatings and substrates.

Verification of the design performance necessitates an appropriate diagnostic capability to assess the thermal response of the optical system to the high power laser beam after it is constructed. Atomic Vapor Laser Isotope Separation (AVLIS) presents a particularly demanding requirement on the design of a high power optical system. High power, high power density, high fluence, multiple wavelengths, mixed polarization, transmissive and reflective optics, and high beam quality requirements are all present simultaneously and are important considerations in the optimum thermal design of the optical train.

High average power thermal effects due to a continuously operating laser are distinct from those associated with single or multiple "single" pulses. Laser pulses are considered single events, provided the time between them is long compared to the time required to dissipate the absorbed energy. Single pulse effects in optical coatings are generally recognized as the result of absorbing inclusions of submicron dimensions between the physically or chemically disturbed substrate surface layer and the thin film coating. See, W. H. Lowdermilk and D. Milam, SPIE, 476, "Eximer Lasers, The Applications and New Frontiers," p. 143 (1984). If these inclusions absorb enough energy during the pulse to heat them to their melting point or boiling point ($10^4$ K.), the resulting thermal expansion, and possible vaporization, creates internal pressures adequate to fracture the polished surface or the coating material of the optical component. These damage sites ma get progressively larger in size as the accumulation of laser pulses continues resulting in an ever increasing deterioration of the optical component.

The damage and thermal effects due to average power is more complicated and is less well understood. Certainly the localized absorption dominant in single pulse damage phenomenology contributes to the average surface absorption. In the continuous or quasi-continuous (high pulse repetition frequency) regime, the inherent absorption, index of refraction and stoichiometry of the coating materials, the details of their film coating design, the coating chamber characteristics, test or operating conditions, e.g. cleanliness, and numerous other process related factors all impact the final average surface absorption of the optical component.

Models for coating absorption are still incomplete. One premise suggests that the primary absorption in thin film coatings takes place at the boundary between the coating and the substrate or the boundaries between the coating layers if there are multiple layers. See H. E. Bennett and D. K. Burge, *J. Opt. Soc. Am*, 70, 268–276 (1980); and O. Arnon, *Appl. Opt.*, 16, 2147–2151 (1977). This premise seems to explain many of the observed phenomena. In this regime the resulting absorption scales with the internal electric field. Multilayer, transmissive coatings create strong periodic electric field maxima deep within the coating due to interference between coating layers. In reflective coatings these electric field maxima diminish exponentially with depth.

In the visible, optical thin film coatings of optical elements have very low thermal mass, while typical glass substrates for the elements have large thermal mass and low thermal conductivity. As the coating heats in response to the applied laser power, the surrounding material responds according to well known heat transfer mechanisms. When the irradiation area is much smaller than the substrate, the majority of the absorbed power is dissipated from the front surface by radiation and convection and very little energy is conducted through the substrate. These fairly typical circumstances present special difficulties in determining the absorption of the coating.

In the past, measurement of surface and bulk absorptions of optical elements were performed by techniques, such as calorimetry or contact thermometry. See A. Hordvik, *Appl. Opt.*, 16, 2827–2833 (1977). These techniques, however, are very difficult to set up and use, and generally require very small test samples to have adequate sensitivity. Calorimetric techniques require heating at the substrate, and unless the heat loss due to radiation conduction and convection is properly included, significant errors in the coating absorption measurements occur. Additionally, this technique is very time consuming. In contact thermometry, using even microscopic thermocouples, conduction by or scattering to the sensor can significantly alter the actual temperature reading and correspondingly the calculated coating absorption.

Another problem is that optics are usually not tested in the environment where they will be used. There is no spatial resolution of surface absorption in vacuum calorimetry, which in the past has used thermocouples to detect temperature rise. Transient heating of coatings has not been measured except for those slow enough to be detected with thermocouples. Until the system of th present invention, there was no practical way to measure the performance of optical elements as actually used in situ with spatial and temporal resolution. Such performance can be recorded on video tape for later analysis or fed directly to a computer for rapid processing.

Advantages of the system of the present invention include real time, non-contact measurement and in situ monitoring of optical elements under operational conditions. Surface absorptions ranging as low as $10^{-5}$ of the incident laser power can be measured with a 50 W test beam. The technique may be used routinely to easily and quickly acquire data for optical coating performance, sensitivity testing, coating development and for quality assessment of purchased optics. More importantly, it can identify hot absorbing coatings that are likely to fail in service or to become optically distorted in operating laser systems.

The system of the present invention contemplates a non-intrusive remote method of measuring the temperature rise of an optical element under high average laser power loading to determine th absorption coefficient. The method comprises irradiating the optical element with a high average power laser beam, viewing the optical element with an infrared camera to determine the temperature across the optical element and calculating the absorption of the optical element from the temperature.

The system of the present invention will be described in more detail hereinafter in conjunction with the drawings wherein:

FIG. 1 is a schematic representation of the system of the present invention;

FIG. 2 is a schematic representation of a visual image produced by the system of the present invention;

FIG. 3 is a schematic representation of a temperature profile produced by scanning the visual image of FIG. 2;

FIG. 4 is a graphical representation of coating applications and a range of coating absorptions observed utilizing the system of the present invention; and FIG. 5 is a further schematic representation of the system of the present invention.

FIG. 1 illustrates the system of the present invention. It shows a high average power laser 10 producing a laser beam 12 which strikes an optical element 14 having an optical coating 16. The coated optical element surface is viewed by an infrared television camera 18. The camera may be an Inframetrics Model 525 thermal imaging camera. It has a spectral range of 2 to 12 microns, a minimum temperature resolution of 0.1° C., multiple range capability, and an adjustable field of view and associated spatial resolution.

FIG. 2 shows the visual output picture of camera 18. This picture is scanned to detect the temperature distribution or profile across the optical element, and then that scan is plotted on a calibrated display shown in FIG. 3. The horizontal lines of the display of FIG. 3 correspond to approximately one degree centigrade (°C.) of temperature rise. The system of the present invention provides a spatially-resolved, thermal distribution (FIG. 2) with convenient linescan profile (FIG. 3) to measure the peak temperature.

Temperature data generated by the system of FIG. 1 was compared to the results of a computer model that accurately simulates the total thermo/structural/optical response of the optical element. The absorption value used in the simulation to achieve the same measured temperature profile, that was measured, is the calculated value for the surface absorption. Obviously, accuracy can only be achieved in this manner if the model is sophisticated enough to account for all of the significant heat transfer mechanisms.

To achieve the requisite accuracy a specialized computer code, TSO (Thermal/Structural/Optical), was written for specific realizable boundary conditions. The program listing for TSO is attached as Appendix A. The code includes a multi-node, finite differencing network that simulates the thermal response of any optical element (transmissive or reflective) of reasonable geometry which is cooled by radiation, conduction and free convection. Verification of the free convection constants and the radiation emissivity constant are determined by independent measurements.

A coating absorption may be deduced from the peak temperature excursion observed. Alternatively, the coating absorption may be deducted by matching the shape of the experimentally observed temperature distribution to the calculated temperature distribution.

Rather than performing a computer analysis for every optical element that is examined, a simple approximate formula was generated to provide rapid in situ results at the time of the thermal measurement. TSO was executed repeatedly over a wide range of surface absorption ($10^{-5} - 10^{-3}$), of power (50-5000 watts), and beam size (0.1-2 cm). It was found that the following simple formula consistently estimated the more accurate computer results to within about 30% over the range of interest:

$$\text{Alpha} = \frac{0.045 * T^{1.11} * R^{0.83}}{p^{1.05}}$$

where:
Alpha=coating absorption,
T=peak temperature (°C.),
R=laser beam radius (cm), and
p=laser power (watts).

Since the surface absorption values vary from component to component by more than an order of magnitude, this simple expression is adequate and is preferred for most surface absorption evaluations.

To test optical coatings being developed for Atomic Vapor Laser Isotope Separation (AVLIS), a VENUS copper and dye laser facility at Lawrence Livermore National Laboratory (LLNL) was utilized. VENUS consists of 32 copper vapor lasers arranged in four master oscillator/power amplifier (MOPA) chains. The copper vapor lasers are configured to optically pump two dye laser chains or to be used directly for testing optics. The total copper laser output is typically 300 watts with a power split of 60/40 between the 511 nm and 578 nm wavelengths. The dye chains, one pumped at 511 nm and the other at 578 nm, have outputs typically 20 and 40 watts and can be tuned from 530 nm to 580 nm.

The AVLIS optical system uses a wide variety of different visible coatings, many of which are especially challenging. Polarization sensitive reflectors are used for beam transport, and high efficiency coatings are required for reflective and transmissive elements. All must operate at high power with a minimum of optical distortion.

Some of the coating applications tested and the range of coating absorptions observed are shown in FIG. 4. Over 180 separate measurements have been performed on coatings from several vendors. Although these results reflect the wide variability in coating absorption performance of optical elements due to different designs, materials and fabrication techniques, there has been a significant (~20 times) reduction in the coating absorption seen in the best broad-band maximum reflectors, and a noticeable but smaller improvement in other coating types. Also as a result of utilizing the present invention, several vendors have been able to reproduce many of the better coating designs on a fairly consistent basis. As suggested above, the data for beamsplitters and polarizers have consistently higher absorption for the transmitted component, but as exemplified by the anti-reflecting coating for the dye laser window, this relatively simple transmissive coating has a surface absorption comparable to the maximum reflectors.

Measurements of the surface temperature of an optical component under optical laser light loading using a thermal imaging camera is an efficient and accurate method to determine the absorption of thin film optical coatings. Using a 50 to 100 watt average power laser and a typical, commercially available IR camera (like Inframetrics Model 525), the lower bound on the coating absorption measurement is $\sim 10^{-5}$. In general, this sensitivity is adequate to evaluate most of the best commercially available coatings.

Among the very low absorption coatings, several anti-reflection coatings were measured that were negligible 5 compared to the bulk absorption contribution of the substrate. When the thermal analysis system described above is applied to heat transfer within the substrate for very small surface heating, the bulk absorption of the substrate can be estimated. In general, most high quality fused silica substrates have a bulk absorption of $2-5\times 10^{-5}$/cm at 600 nm. Utilizing this information, the substrate and coating absorption may be selected to match the shape of the temperature profile across the optical element.

Perhaps the greatest utility for the remote sensing system of the present invention is the in situ, observation of an operating, high power laser system to identify hot optical components. For example, during the activation phase of the Laser Demonstration Facility (LDF) at LLNL the operating laser system was routinely surveyed to find poor quality or dirty optical components The technique of the present invention was also particularly sensitive in finding thermal problems in optical mounts that were heated by relatively low intensity scattered light.

The foregoing description of the preferred embodiment of the invention has been presented for purposes of illustration and description. It is not intended to be exhaustive or to limit the invention to the precise form disclosed, and obviously many modifications and variations are possible in light of the above teaching. The preceding embodiment was chosen and described in order to best explain the principles of the invention, and its practical application to thereby enable others skilled in the art to best utilize the invention in the described embodiments, and with various modifications as are suited to the particular use contemplated. It is intended that the scope of the invention be defined by the appended claims.

What is claimed is:

1. A method for measuring absorption of an optical element comprising:
    irradiating the optical element with a high average power laser beam to increase a temperature thereof;
    examining the surface of the optical element to determine the infrared energy being emitted therefrom as a result of the increase in temperature;
    determining the temperature across said optical element from said examination; and
    calculating the absorption of the optical element from said temperature.

2. A method for measuring surface absorption of an optical element comprising:
    irradiating the optical element with a high average power laser beam to increase a temperature thereof;
    examining the surface of the optical element with an infrared device to produce a representation of the temperature cross the optical element;
    determining the temperature across said optical element from aid representation; and
    calculating the surface absorption of the optical element rom said temperature.

3. The method of claim 2 further including producing from said representation a temperature distribution across said optical element.

4. The method of claim 2 further including calculating the surface absorption, utilizing a formula comprising:

$$\text{Alpha} = \frac{0.045 * T^{1.11} * R^{0.83}}{p^{1.05}}$$

where:
    Alpha=coating absorption,
    T=peak temperature (°C.),
    R=laser beam radius (cm), and
    p=laser power (watts).

5. The method of claim 2 further including selecting the surface absorption to match a peak temperature excursion observed.

6. A method for measuring surface absorption of an optical element, comprising:
    irradiating the optical element with a high average power laser beam to increase a temperature thereof;
    examining the optical element with an infrared device to produce an image of the optical element;
    determining the temperature across said optical element from said image; and
    calculating the surface absorption utilizing a formula comprising:

$$\text{Alpha} = \frac{0.045 * T^{1.11} * R^{0.83}}{p^{1.05}}$$

where:
    Alpha=coating absorption,
    T=peak temperature (°C.),
    R=laser beam radius (cm), and
    p=laser power (watts).

7. The method of claim 6 further including producing from said image a temperature distribution across said optical element.

8. A method for measuring surface and/or bulk absorption of an optical element in a high average power laser beam comprising:
    irradiating the optical element with a high average power laser beam to increase a temperature thereof;
    viewing the surface of the optical element with an infrared camera;
    producing a picture from said camera;
    scanning the picture to determine a temperature profile across said optical element; and
    matching the temperature profile by proper selection of surface and bulk absorption of the optical element.

9. A system for measuring absorption of an optical element comprising:
    an infrared camera to view the surface of the optical element to produce an image of the infrared energy being emitted therefrom when irradiated with a high average power laser beam;

means for determining from a image a temperature profile across said optical element; and means for calculating the absorption of the optical element from said temperature profile.

10. A method for measuring absorption of an optical element comprising:

irradiating the optical element with a high average power laser beam to increase the temperature thereof;

producing a representation of the temperature across the optical element;

determining the temperature across the optical element from representation; and calculating the surface absorption utilizing a formula comprising:

$$\text{Alpha} = \frac{0.045 * T^{1.11} * R^{0.83}}{p^{1.05}}$$

where:

Alpha = coating absorption,

T = peak temperature (°C),

R = laser beam radius (cm), and p = laser power (watts).

11. A system for measuring absorption of an optical element comprising:

means for irradiating the optical element with a high average power laser beam to increase the temperature thereof; means for producing a representation of the temperature across the optical element;

means for determining the temperature across the optical element from said representation; and means for calculating the surface absorption utilizing a formula comprising:

$$\text{Alpha} = \frac{0.045 * T^{1.11} * R^{0.83}}{p^{1.05}}$$

where:

Alpha = coating absorption,

T = peak temperature (°C),

R = laser beam radius (cm), and p = laser power (watts).

* * * * *